United States Patent [19]

Danzig

[11] Patent Number: 4,667,671

[45] Date of Patent: May 26, 1987

[54] APPARATUS FOR LIGATING BLOOD VESSELS, NERVES AND OTHER ANATOMICAL STRUCTURES

[76] Inventor: Fred G. Danzig, 573 Second St., Brooklyn, N.Y. 11215

[21] Appl. No.: 798,425

[22] Filed: Nov. 15, 1985

[51] Int. Cl.[4] ............................................. A61B 17/12
[52] U.S. Cl. .................................. 128/325; 128/322; 128/346
[58] Field of Search ............... 128/325, 326, 346, 321, 128/322; 251/9, 10; 227/DIG. 1; 72/410

[56] References Cited

U.S. PATENT DOCUMENTS

| | | | |
|---|---|---|---|
| 2,301,622 | 11/1942 | Hambrecht | 128/325 |
| 3,106,919 | 10/1963 | Churchville | 128/346 |
| 3,247,852 | 4/1966 | Schneider | 128/346 |
| 3,270,745 | 9/1966 | Wood | 128/325 |
| 3,323,208 | 6/1967 | Hurley | 128/346 X |
| 3,503,397 | 3/1970 | Fogarty et al. | 128/346 X |
| 3,581,551 | 6/1971 | Wilkinson | 128/325 X |
| 3,916,908 | 11/1975 | Leveen | 128/346 |
| 4,060,089 | 11/1977 | Noiles | 128/325 |
| 4,120,302 | 10/1978 | Ziegler | 128/322 |
| 4,506,671 | 3/1985 | Green | 128/334 R |

*Primary Examiner*—Michael H. Thaler
*Attorney, Agent, or Firm*—Eliot S. Gerber

[57] ABSTRACT

Apparatus for ligating blood vessels, nerves or other anatomical structures, such as Fallopian tubes, utilizing a modified form of a standard hemostat, including a removable pair of hemostat jaw inserts of non-toxic, substantially rigid material, each releasably secured to a jaw of the hemostat, each insert having removably formed therein at least one clip member, locking structure contained by at least one of the clip members adapted lockingly to engage the other of the clip members, whereby the jaws of the hemostat can be opened to any desired width and then closed, locking the clip members to form a ligating clip over or in a blood vessel or other anatomical structure and opening the jaws causes the joined clip members to break away from the inserts.

A method of using said apparatus and process comprising the steps of removably locking the inserts on the jaws of a hemostat, opening the jaws to any desired width and placing the jaws on opposed sides of a blood vessel, nerve or other anatomical structure to be closed, closing the jaws, engaging the locking structure of the clip members on either side of the anatomical structure, opening the jaws to break away the clip members from said inserts and leaving the clip members in locking engagement on or in the blood vessel or other anatomical structure.

5 Claims, 25 Drawing Figures

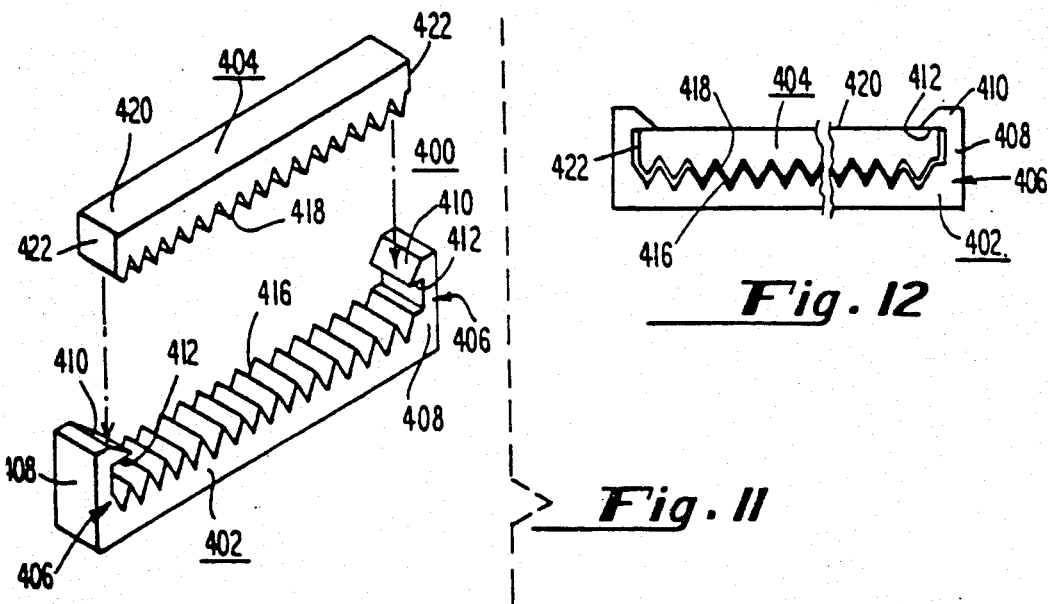
Fig. 12
Fig. 11
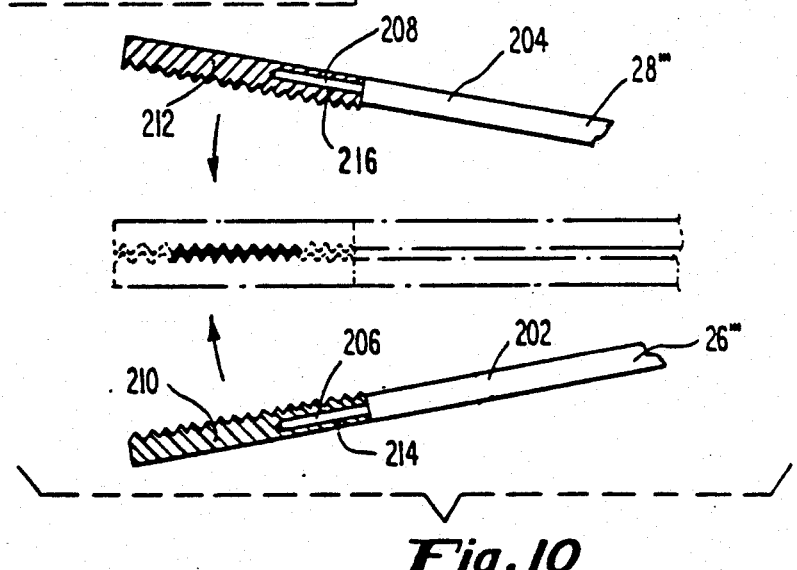
Fig. 10
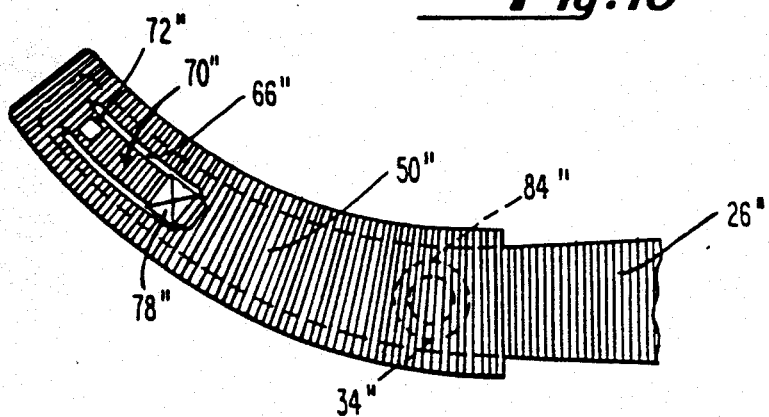
Fig. 9

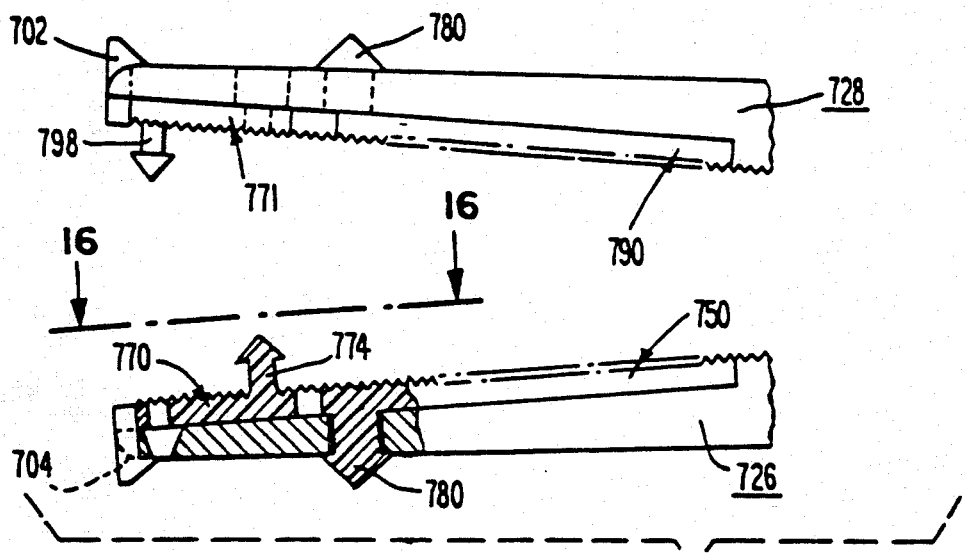
*Fig. 15*
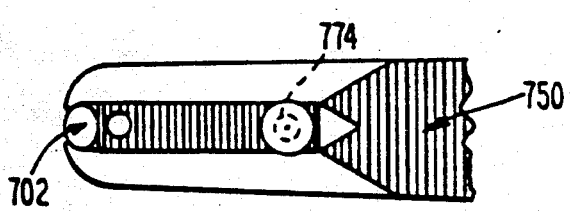
*Fig. 16*          *Fig. 17*
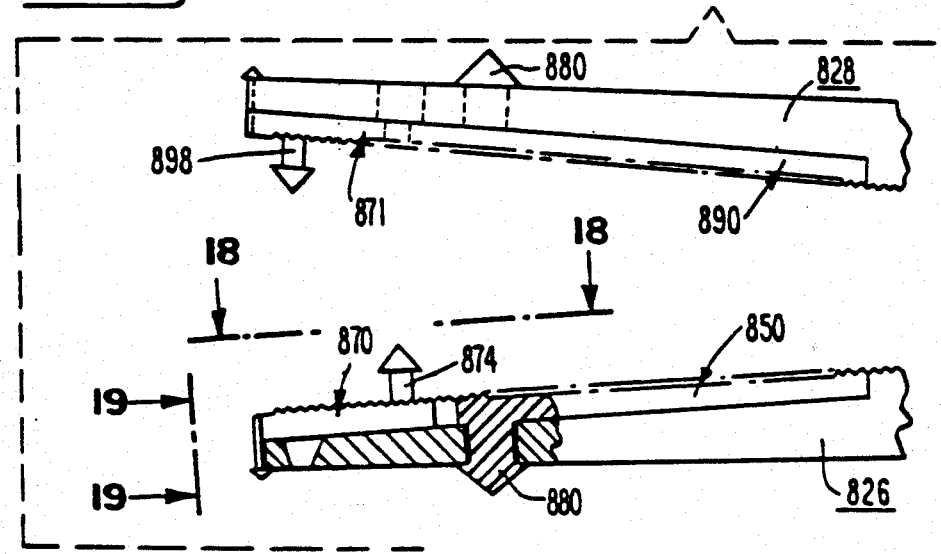
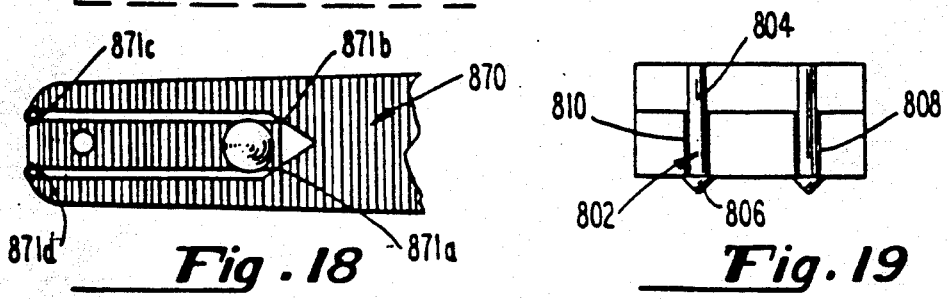
*Fig. 18*          *Fig. 19*

APPARATUS FOR LIGATING BLOOD VESSELS, NERVES AND OTHER ANATOMICAL STRUCTURES

BACKGROUND OF THE INVENTION

1. Field of the Invention

The invention relates to surgical clips and hemostat constructions therefor, for the purposes of ligating (closing off) blood vessels, nerves or other anatomical structures during a surgical or other medical procedure on a human being or other animal.

2. State of the Art

The conventional method for ligating blood vessels or other anatomical structures utilizes the tying off, with a thread, of the blood vessels or other structures. Since a surgical procedure can be characterized as a struggle against bleeding, quickness and certainty are important for sealing off the cut end of a blood vessel. It is also always desirable to make any surgical procedure as brief as possible for the convenience of the patient and the economical use of the time of medical personnel and facilities. The string ligation technique is undesirable, because of the time which it takes, the requirement that two persons be involved in the ligation procedure and the sometime difficulty of access to remote anatomical locations for string ligating.

Some surgeons have adopted the use of metal clips in lieu of such string ligation procedures. Metal clips of th type most commonly used currently are disclosed and illustrated in U.S. Pat. No. 3,363,628, and an applicator construction illustrating a method of application of such a metal clip is illustrated in U.S. Pat. No. 3,326,216.

Other types of metal clip constructions are illustrated in U.S. Pat. Nos. 3,270,745, 3,347,239, 3,867,944 and 3,439,522. Still other types of clips and applications therefor are illustrated in U.S. Pat. Nos. 3,954,108, 3,882,854, 3,924,629 and 3,856,016.

Although the commonly used metal clips comprise, in some respects, an advance over the prior art of ligation they do possess several substantial disadvantages. The metal clips are quite small, on the order of 3 mm. or more in length, and are difficult to handle. A primary disadvantage is the inconvenience of and time consumed in placing the clip in the applicator and placing the clip over the blodd vessel before closure. Also, metal clips occasionally drop into the surgical opening and may be difficult to locate and remove.

One shortcoming of the prior art use of small metal clips may be understood by the analogy of attempting to thread a needle having a small eye. It is difficult to get the thread through the needle because of the size of the eye. Similarly, the U-shape of the surgial clips of the prior art and their extremely small size and opening makes it difficult to get the clip accurately placed in proper position over the blood vessel before closure. This difficulty means that the use of the clips of the prior art is relatively time-consuming and therefore undesirable because of the timportance of shortening the duration of surgery as much as possible.

The instant invention, when compared to the prior art, may be analogized to the use of a needle with a large eye being threaded with the same piece of thread. The large eye facilitates the insertion of the thread therethrough. Similarly, the fastening of the inserts (sometimes also referred to as clip assembly members) to hemostat jaws provides a greater opening for movement with respect to the structure being ligated.

An important advantage of this invention is that it reduces the ligation procedure from two steps to one step, since the placing of the hemostat over the blood vessel to close off flow in the blood vessel automatically closes and locks the clip members in place, so that when the hemostat is opened up and removed the clip is automatically left in place, avoiding the necessity of a second step to place a metal clip in place or to otherwise ligate the vessel.

BRIEF SUMMARY OF THE INVENTION

The invention is directed to a surgical clip construction comprised of two discreet clip members and inserts carrying each of said clip members, an applicator therefor, and a method of ligating blood vessels and other anatomical structures in human beings and other animals using the hemostat and clip construction of this invention.

The applicator is desirably a modified form of the conventional types of hemostats, part of the jaws of which have been removed to accommodate the insert, so that the modified hemostat of this invention is used by the surgeon or surgical nurse in the smae manner as conventional hemostats are used for the purpose of closing a blood vessel or other anatomical structure.

In one embodiment of the invention, the insert carrying a clip member is seated in a cut-out portion of the modified hemostat jaw, and in another embodiment of the invention the insert forms the distal end of the hemostat jaw. The insert is of such size and design as to be easily handled and readily and lockingly attached to the modified hemostat.

Each insert has a break-away surgical clip member formed therein, and each of the two cooperating inserts of a single unit has, in face-to-face relation to the other, a surgical clip member formed therein or attached thereto. The surgical clip members are weakly connected to the inserts at one or more locations, where they are firmly held in place but can easily break away from the inserts. The clip members are provided with suitable locking means, such as male and female members, which may be located on one or both of the clip members to engage the opposite clip member to lock the clip members in place on either side of the blood vessel or other anatomical structure.

Each insert and corresponding clip member is desirably injection molded as a single unit of a suitable substantially rigid, non-toxic, pharmaceutically acceptable polymeric material, chosen for proper characteristics of rigidity, resilence or snapability or other appropriate characteristic for locking of the male and female members, ease of separation at the breakaway points and ease and economy of fabrication. In an embodiment of the invention, the surgical clip members may be formed of a suitable material which will ultimately dissolve in the body after the structure has, for example, sealed itself closed. Several alternative embodiments of the invention are illustrated utilizing different types of locking means for locking the two clip members together. It is desirable that the plastic material of which the inserts and clip members are made be substantially rigid, in order to prevent any significant deformation of th clip when located in place, which could cause leakage, but is somewhat bendable to conform to the shape of the structure being closed. Depending on the locking construction used in any given clip embodiment, the clip plastic material must have sufficient resilience or "snapability", more fully described below, to provide an effective lock.

In the method of the invention, the jaws of a modified form of hemostat including inserts having breakaway locking clip members are placed about a blood vessel, nerve or other anatomical structure to close the same and prevent fluid flow, if any, therethrough. The jaws of the hemostat are completely closed, locked in position if desired and then opened, thereby leaving a surgical clip locked in place by virtue of the closing and opening of the modified hemostat.

OBJECTS OF THE INVENTION

It is therefore an object of this invention to provide a safe and effective surgical clip construction which may be used quickly and easily.

Yet another object of this invention is to provide a surgical clip construction which may be used with a modified form of conventional hemostat, where each clip member is part of a jaw insert of the hemostat, so that the jaws may be opened as wide as possible to locate the blood vessel or other anatomical structure with respect to the clip members, before the jaws of the hemostat are closed to lock the clip members in place.

A further object of this invention is to provide a surgical hemostat and clip construction, whereby the jaws of the hemostat are modified to incorporate two inserts, each including a breakaway clip member, so that the hemostat may be applied to a freshly cut blood vessel, for example, and, when removed, leave a locked surgical clip in place.

A still further object of this invention is to provide a surgical clip construction which is inexpensive, easy to use, and reduces the time necessary to occlude the blood vessel or other anatomical structure.

Another object of this invention is to provide a surgical clip construction of a soluble polymeric or other material, which will dissolve after it has outlived its usefulness.

Yet another object of this invention is to provide a surgical clip construction and modified form of hemostat which, in use, is virtually identical to the conventional form of hemostat, so that it is most convenient for use by the medical profession.

Still another object of this invention is to provide a surgical clip construction which can easily, quickly, safely and effectively be inserted in the jaws of an applicator which resembles a conventional hemostat.

An additional object of this invention is to provide a quick, easy and safe method for applying surgical clips to blood vessels, nerves and other anatomical structures.

These and other objects of this invention will readily be perceived from the following detailed description of the invention, when read in connection with the appended drawings, in which like numerals designate like parts.

DESCRIPTION OF THE DRAWINGS

FIG. 9 is a top plan view of the lower jaw insert of an embodiment of the invention, similar to that illustrated in FIGS. 1 to 6, modified for a hemostat with curved jaws;

FIG. 10 is a schematic view, partly in cross-section, showing a modified form of hemostat jaw insert, where the hemostat jaws are shortened and the jaw inserts form extensions of the hemostat jaws;

FIG. 11 is a perspective view of another embodiment of the surgical clip of this invention;

FIG. 12 is a side elevational view of the surgical clip of FIG. 11 in closed position;

FIG. 15 is a side elevational view similar to FIG. 2, partly in cross-section, of yet another embodiment of the jaw insert of this invention;

FIG. 16 is a top plan view, taken along line 16—16 of FIG. 15;

FIG. 17 is a side elevational view similar to FIG. 2, partly in cross-section, showing yet another embodiment of the jaw insert of this invention;

FIG. 18 is a top plan view, taken along line 18—18 of FIG. 17;

FIG. 19 is a front elevational view, taken along line 19-19 of FIG. 17;

DETAILED DESCRIPTION OF THE INVENTION

Figure 1:
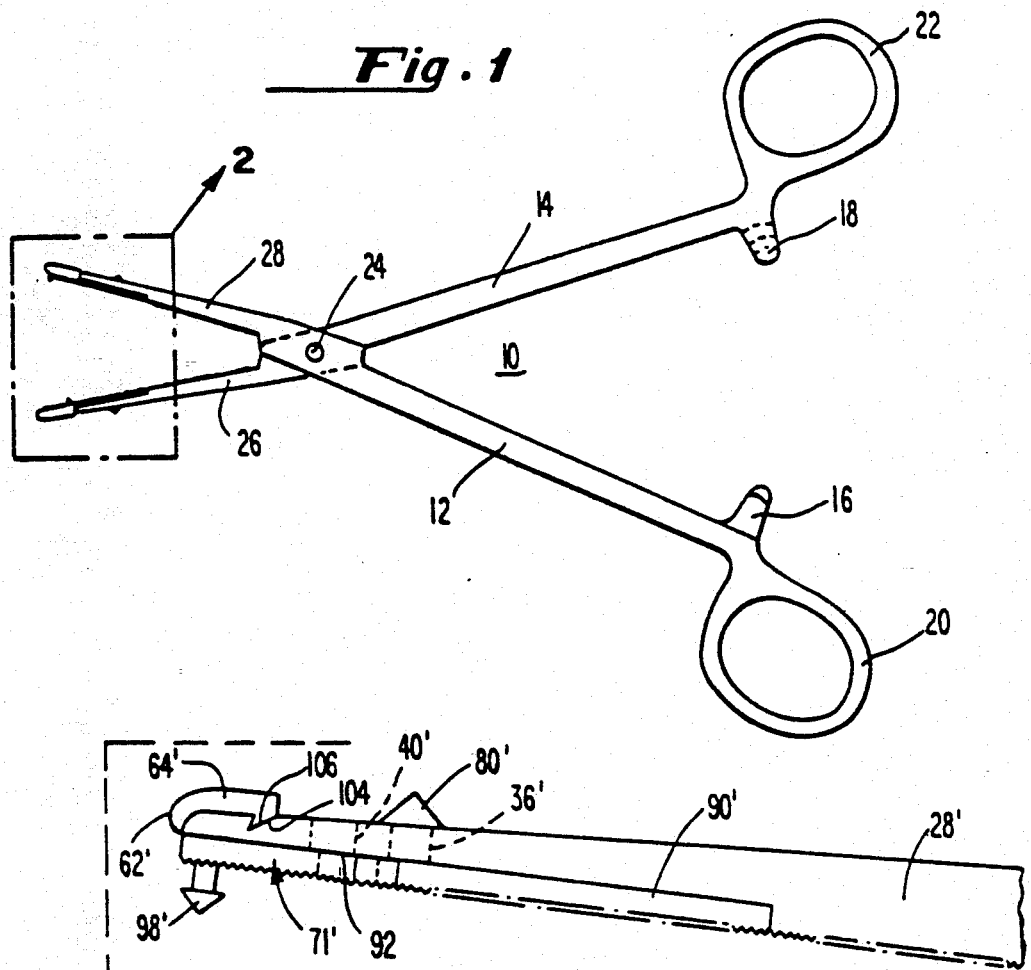
FIG. 1 is a side elevational view of a modified form of hemostat of this invention.

Viewing FIG. 1, there is illustrated a modified hemostat in accordance with this invention and generally designated by the numeral 10. The hemostat 10 is of a type which is generally well known in the art, is made of surgical steel or similar materials, and is comprised of handles 12 and 14, releasable locking members 16 and 18 and finger grips 20 and 22. The two handles are rotatably connected by pin 24 and terminate in jaws 26 and 28. Hemostats come in numerous sizes and shapes and, as more fully described below, the components of this invention can be adapted for application to any size or shape of hemostat.

Hemostats modified in accordance with the principles of this invention may have a cut-out portion in each jaw adapted to seat a suitable insert, sometimes referred to as a clip assembly member, of which the clip member is a part. For example, viewing FIG. 2, hemostat jaw 26 has a cut-out 27 defined by its upper surface at the distal end thereof, and also differs from a conventional hemostat by having apertures 34 and 38 extending through the jaw. The jaw 26 has a serrated upper surface 30. The purpose of the serrations is to permit the peaks of the serrations of one jaw to project into the valleys of the serrations of the opposing jaw and thereby provide a better locking grip on whatever is being grasped by the hemostat in the closed position.

Figure 2:
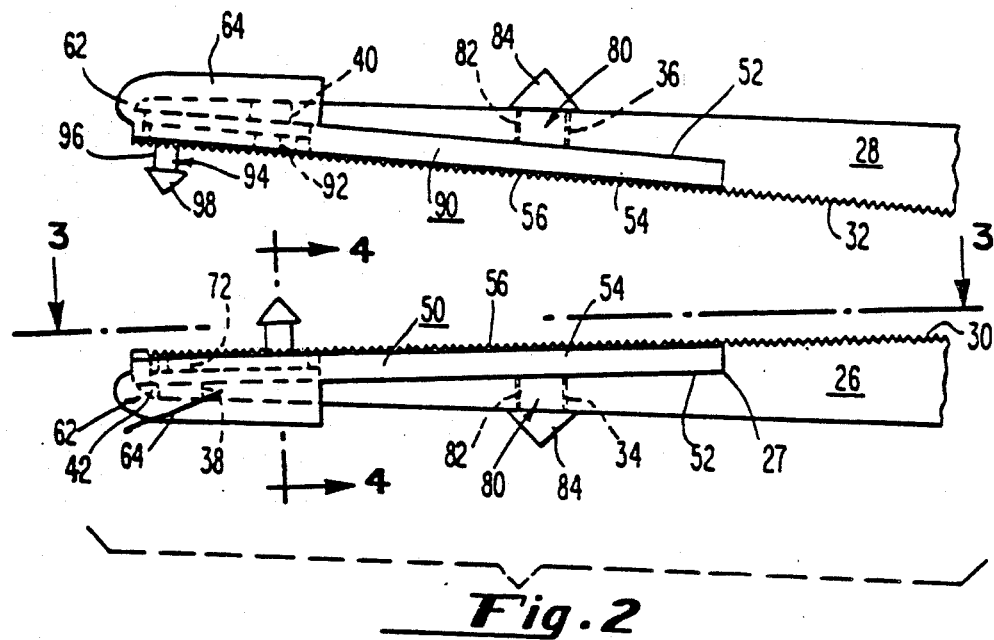
FIG. 2 is an enlarged view of the distal ends of the jaws of the hemostat of FIG. 1.
Figure 3:
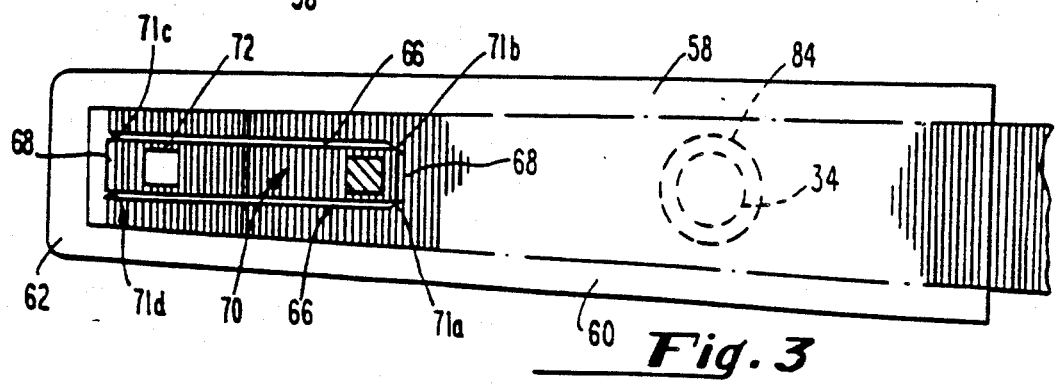
FIG. 3 is a top plan view of the insert and jaw of this invention, taken along line 3—3 of FIG. 2.

Seated in hemostat jaw 26 is jaw insert member 50. The insert 50, as best seen in FIGS. 2 and 3, is an elongated, generally rectangular member, terminating at its end in a rounded tip 62 and a sleeve member 64. Insert 50 has a serrated upper surface 56, abutted on its two long edges by the somewhat recessed edge members 58 and 60. The serrations 56 on upper surface 54 of the insert may be of the same size, spacing and depth as the serrations 30 of the lower jaw 26, and are intended to function in the same manner as the serrations of a conventional hemostat. Insert 50 has a lower surface 52 which is seated in the cut-out 27 of the hemostat jaw 26.

Protruding from and forming an integral part of insert 50 is a dart or locking member 80 which extends downwardly through aperture 34 in the hemostat jaw. Locking member 80 helps secure insert 50 to the jaw 26. The dart 80 comprises a shaft portion 82 and an enlarged head 84. In the illustrated embodiment the enlarged head 84 has a pyramidal shape, of square cross-section, although the shape of the head may vary as more fully described below. The maximum dimension of head 84 is greater than the maximum dimension of aperture 34. The "snapability" characteristic of the head 84 and aperture 34 is necessary in order to allow the head to enter and pass through aperture 34, after which head 84 expands and aperture 34 contracts to lock an end of insert 50 to the jaw 26.

The end of insert 50 at the distal end of jaw 26 is locked to the jaw 26 by the sleeve 64, which overlies the distal end 42 of jaw 26, so that the distal end of the jaw 26 slides into the sleeve 64 and the distal end of the jaw 26 is securely held within the sleeve by a close fit, although a positive locking means may also be used, as illustrated in other embodiments of the invention.

Forming part of the insert 50, and connected thereto only at the four corners 71a, 71b, 71c and 71d, by breakaway point contacts, is the clip member 70. In the embodiment illustrated, the clip member 70 is elongated and rectangular. Except for the four connections noted above, where the clip member 70 is attached to the insert 50, it is separated from the insert 50 by spaces 66 at its opposite sides and 68 at its opposite ends. The connecting portions 71a, 71b, 71c and 71d are very thin and rigid and may be point connections or thin, perforated or non-perforated webs, so that the clip member 70 will easily break away from insert 50 as more fully described below.

Figure 6:
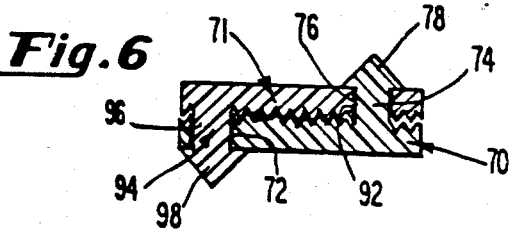
FIG. 6 is an enlarged view of the surgical clip of FIG. 5.
Figure 4:
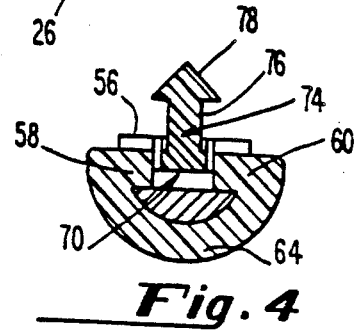
FIG. 4 is a cross-sectional view, taken along line 4—4 of FIG. 2.

As seen in FIGS. 4 and 6, clip member 70 is formed with an integral male member 74 at one end. Male member 74 has an upstanding shaft 76 of square cross-section terminating in an enlarged pyramidal head 78. At the other end of the clip member 70 is an aperture 72, positioned and adapted lockingly to be engaged by a corresponding shaft 96 and head 98 of male member 94 on the opposing clip member 71.

Jaw 28 of hemostat 10 is similar to jaw 26, except that the cut-outs and apertures are opposed to the corresponding cut-outs and apertures on jaw 26. Jaw 28 has serrated surfaces 32 and the serrations 56 of jaw insert 90, which is seated on jaw 28, may correspond in size, shape and spacing to the serrations 32, in similar manner to the serrations on the jaw 26 and insert 50.

Jaw 28 has apertures 36 and 40 extending through it. The purpose of these apertures is the same as that of apertures 34 and 38 in jaw 26. Insert 90 has a rounded tip 62 and a sleeve 64 which engage the distal end of jaw 28 in the same manner as rounded tip 62 and sleeve 64 engage jaw 26, as seen in FIG. 2.

Forming a part of insert 90 is a clip member 71 which is almost identical with clip 70, except for the placement of the respective male and female members 94 and 92. The male members 74 and 94 may, if desired be located at or near the ends of the clip members on which they are formed, but the apertures 72 and 92 must be spaced from the ends of the clip members. Insert 90 has a protruding male member 94 proximate the distal end of jaw 28, in juxtaposition with the aperture 72 in clip member 70. Male member 94 has a shaft 96 and enlarged head 98, which are of the same size and dimensions as the corresponding parts of male member 74. Clip member 71 similarly has an aperture 92, of the same size and shape as aperture 72, and adapted lockingly to admit male member 74 to join one end of clip member 70 to the juxtaposed end of clip member 71.

In operation, the foregoing embodiment of the invention functions as follows. The specially designed hemostat 10 is initially in the unloaded condition, so that its jaws 26 and 28 do not contain a set of inserts 50 and 90, and the inserts would be first loaded onto the corresponding jaws. This step could be done manually or automatically, the inserts being taken from a suitable sterile container or package, where they may be packaged individually or in bulk, and loaded onto the sterile hemostat 10.

The insert 50 and 90 may each desirably be at least about 10 mm. in length, and one reason for this length is to make the inserts of a size that can easily be handled manually, the end sleeves able to be placed quickly and easily over the respective jaws so that the distal ends of the hemostat jaws, respectively 42 and 44, engage in the corresponding sleeves 64 of the two inserts.

After the distal ends of the jaws have been slid into their corresponding sleeves, the male members or darts 80 are pressed into the respective apertures 34 and 36, heads 84 of the male members thereby engaging and locking inserts 50 and 90, respectively, into jaws 26 and 28. The inserts 50 and 90 are then securely fastened in place.

In preparation for surgery, a nurse or nurse's aid can pre-load a large number of modified hemostats of this invention with inserts in accordance with this invention, so that no time is taken during the surgical procedure for loading the surgical clips into or on the hemostat.

Although the inserts of this invention may be loaded manually onto or into the jaws of the modified hemostats of this invention, it is preferred that the loading be done by the use of a suitable magazine (not shown). The magazine would be loaded with one or more pairs of inserts in spaced opposition to each other and separated by a suitable rigid member which keeps the clip members from locking during the loading operation. The magazine could be formed with two opposed outer surfaces, each defining grooves to guide the hemostat jaws to the inserts. The hemostat jaws (in the embodiment of FIGS. 1 to 6, for example) would be inserted in the magazine grooves at an angle which corresponds to the angle of the magazine's loading faces, the distal ends of the jaws would be inserted in the corresponding jaw-engaging sleeves of the inserts and the male members of the inserts would be snapped into place in the corresponding apertures of the hemostat jaws. The hemostat would then be removed from the magazine with the inserts in place, ready for use.

The magazines may be pre-packaged in sterile condition to ensure the sterility of the inserts and clip members in use.

The hemostat is then placed in a suitable tray, readily accessible for use when needed. Whenever surgery is in progress, and, for example, blood vessels are being cut and must immediately be closed off to prevent bleeding, the surgical clips and hemostats of the invention are immediately ready. The surgeon, an assistant, or other medical professional who is closing off the blood vessels will take a suitable size and shape of hemostat, for example hemostat 10, and pinch the blood vessel between the portion of the jaws of the hemostat where clip members 70 and 71 are located. The jaws of the hemostat can be opened to any desired width, thereby to facilitate the placement of the blood vessel between the opposing clip members 70 and 71. The handles 12 and 14 of the hemostat would then be closed, and locking members 16 and 18 would lock the hemostat in the closed position. In this situation, the unit is in the position illustrated in Figure 5, where the jaws 26 and 28 are closed, and the corresponding peaks and valleys of the teeth 30 and 32 of the jaws and teeth 56 of the inserts are seated adjacent to each other. Between the clip assembly members now joined the blood vessel or other anatomical structure being closed off is sealingly seated.

When the respective male members 74 and 94 lock in their corresponding apertures 92 and 72, the heads 78 and 98 occupy, in part, the space created by the apertures 40 and 38 in the respective jaws of the hemostat. In this locked position, the hemostat may be allowed to remain in place for as long as desired. When it is desired to remove the hemostat, the locking members 16 and 18 are unlocked, in the normal and usual manner, and the handles 12 and 14 are separated. The force which keeps the two clip members locked together, by virtue of the engagement of male members 74 and 94, and the force which keeps the inserts 50 and 90 fastened to the jaws, is greater than the force needed to separate the four corners 71a, 71b, 71c and 71d which connect clip member 70 to insert 50 and the four similar corners connecting clip member 71 to insert 90, so that when the jaws 26 and 28 of the hemostat are closed and then opened, the clip members 70 and 71 break away from the inserts, allowing the hemostats to be removed, while leaving the surgical clip locked in place about the blood vessel or other anatomical structure.

The heads 78 and 98 may be made sufficiently sharp and rigid to be able to pierce tissue. Therefore, the surgical clips of the invention can be used to pierce the structures to which they are applied, providing an even better ligation than otherwise could be the case. The clip could also be used to tie off areas of human tissue other than discrete tubular members or nerves such as a bleeding surface.

It is notable that the process set forth above can be varied without departing from the spirit and scope of the invention. For example, inserts 50 and 90 need not be inserted in the jaws of the hemostat prior to the surgical procedure; they can be inserted when needed. Furthermore, the hemostat can be removed immediately after the blood vessel is closed off and need not be left in place for any period of time after the clip members are locked in place.

The inserts 50 and 90 and clip members 70 and 71 may be formed as a single, integral unit of one material for ease and economy of fabrication. The material must be substantially rigid to allow the male members to form a secure locking engagement of the two clip members and securely to hold closed any structure to which the clip members are applied. The clip members should be sufficiently bendable to be able to bend around and substantially conform to the blood vessel or other anatomical structure being ligated with the clip of this invention.

The material fo the clip members must also possess the ability for heads of the male members 78 and 98 and their corresponding apertures 72 and 92 to deform when the heads enter the apertures, so that the enlarged portion of the head may pass through the smaller aperture to form a locking engagement. This characteristic is known in the art as "snapability" and is necessary when the type of locking construction shown in FIGS. 1 to 6, for example, is used. If, on the other hand, the locking arrangement of FIGS. 11 and 12 is used, snapability is not essential for the clip members; rather some resilience is required, so that the fingers 406 will initially bend out of the way during closure of the clip members and then lock in place as seen in Figure 12.

The material of the clip members must also be non-toxic and capable of residing inside a human or other animal body, as the case may be, for prolonged periods of time without any deleterious effects. The material must also be susceptible to sterilization, such as by the use of ethylene oxide or steam.

Although any number of polymeric materials, have the desirable characteristics, particularly desirable such materials are known by the trademarks "Delrin" and "Celcon," which are products of E.I. du Pont de Nemours & Company and Celanese Corporation, respectively, Both are acetal resin base polymeric resins of polyformaldehyde, "Delrin" being a homopolymer and "Celcon" being a copolymer. Among the properties which make "Delrin" desirable are: high mechanical strength and rigidity, excellent fatigue endurance, resistence to moisture and other solvents, excellent dimensional stability, ease of fabrication, resiliency, natural lubricity and a reasonably high melting point. Some specific values for the physical properties possessed by "Delrin" include: a tensile strength of 10,000 pounds per square inch (at 0.2 in./min. and at 73° F.), a tensile secant modulus of 520,000 pounds per square inch (at 1% strain, 0.2 in./min. and 73° F.), a flexurol yield strength of 14,100 pounds per square inch at 0.05 in./min. and 73° F.), a compressive modulus of 670,000 pounds per square inch (at 0.05 in./min. and 73° F.), a compressive stress of 5,200 pounds per square inch at 1% def. and 18,000 pounds per square inch at 10% def. (both at 0.05 in./min. and 73° F.), a shear strength of 9,500 pounds per square inch (at 73° F.), a coefficient of linear thermal expansion of 0.000055 inches per inch per degree Fahrenheit, a specific gravity of 1.4 and a melting point of 347 degrees Fahrenheit. Furthermore, these resins are particularly suited to injection molding with either plunger or screw type molding machines although the screw injection machine is preferred. The properties of these resins make possible snap and press-fitting assembly techniques, thereby providing a simple, economical, and rapid means of assembling members of these resins to other plastic materials or metals. In addition, "Delrin" has been fed to rats for 91 days at a dietary level of 25 percent and no significant differences between control and test rats in body weight, food consumption, food efficiency or clinical history resulted therefrom. Moreover, hematological and pathological studies disclosed no changes attributable to the feeding of such resin.

It may be desirable to form the insert of one material and the clip member of another material. For example, it may be desired to form the inserts of plastic and the clip members of metal and to fasten them together in breakaway fashion by the use of an adhesive. The metal may be formed with suitable locking means to provide a proper closure of the clip members. In addition, the various components of the clip members, such as the male members' heads, may be formed of different materials from the other components. However, for economy and ease of fabrication, one plastic material is preferred.

If desired, a radioopaque material can be incorporated in or applied to the polymer from which the clip members are fabricated, so that the clips may be seen on an X-ray.

Figure 22:
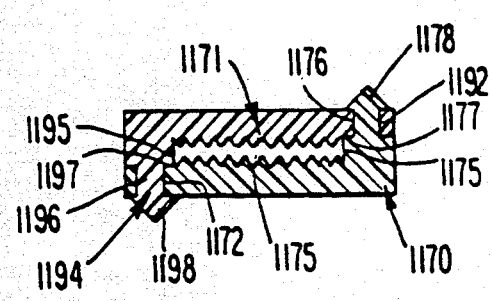
FIG. 22 is an enlarged vertical cross-sectional view of another embodiment of the surgical clip of this invention similar to that illustrated in FIGS. 1 to 6, modified to include a separation in the locked position shown.

FIG. 22 shows an embodiment of the clip members similar to those in FIGS. 1 through 6. The clip member 1170 has in this instance an upstanding shaft that is comprised of two sections 1176 and 1175 as opposed to the single shaft 76 of clip member 70 as illustrated in FIGS. 4 and 6. Clip member 1171 also has a dual section upstanding male shaft 1195 and 1196. The purpose of these dual shafts is to prevent the inner nonplanar surface of clip member 1170 from touching the inner nonplanar surface of clip member 1171 thereby creating a space 1175 between the two interlocked clip members. In actual operation male head 1178 of clip member 1170 deformingly enters and lockingly passes through female aperture 1192 of clip member 1171. The passage of male shaft 1176 through said aperture is stopped when the upper surface 1177 of the larger lower section of the upstanding male member 1175 reaches aperture 1192. Similarly, male member 1194 has a male shaft comprised of two sections 1196 and 1195 of differing sizes. When male head 1198 deformingly enters and passes through aperture 1172 of clip member 1170 its passage is stopped, after it has passed therethrough and lockingly engaged clip member 1170, by surface 1197 of the larger section of male shaft 1195. Thus surfaces 1197 and 1177 prevent the nonplanar surfaces of the two clip members 1170 and 1171 from coming together, thereby creating space 1175. This clip member embodiment is especially useful in that it will cause only minimal trauma to the anatomical structure being occuluded.

Figure 7:
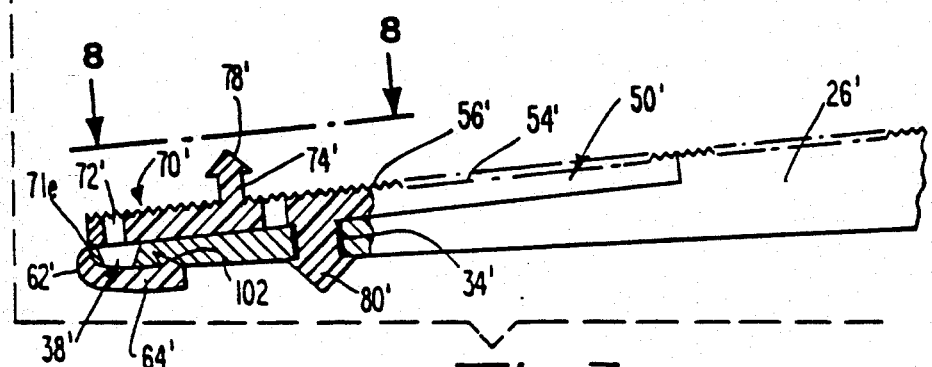
FIG. 7 is a view, similar to FIG. 2 and partly in cross-section, of another embodiment of the jaw insert and surgical clip construction of this invention.
Figure 8:
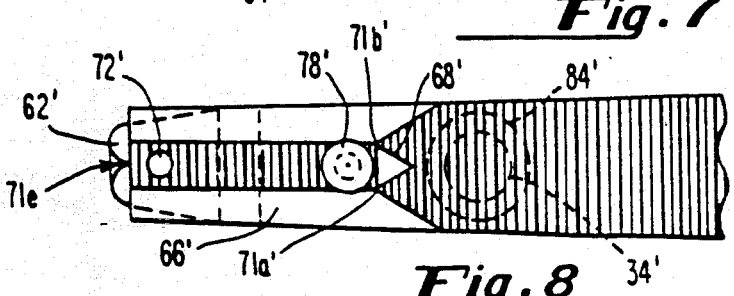
FIG. 8 is a top plan view taken along line 8—8 of FIG. 7.

FIGS. 7 and 8 show another embodiment of the insert and clip member construction of the invention. The clip members of FIGS. 7 and 9 are similar to those of FIGS. 1 to 6. The heads 78' and 98' of the clip members 70' and 71' are conical, rather than pyramidal as shown in FIGS. 1 to 6, and their mating female apertures 72' and 92' are therefore circular in cross-section. Each of the hemostat jaws, respectively designated 26' and 28', has a dart-like aperture, respectively designed 102 and 104, formed in its outer surface near its distal end.

The tip engaging members 64' are pointed at their ends 62', as seen in FIG. 8, and each terminates in an inwardly extending elongated dart-like member 106, which engages into aperture 102 or 104, as the case may be, to facilitate the locking in place of the respective inserts. In the embodiment of FIGS. 7 and 8, the locking members 80' and the corresponding apertures 34' and 36' in jaws 26' and 28' are shown as located close to the distal end of the jaws, in order to provide greater restraint proximate to clip members 70' and 71', although their precise location is a matter of choice.

As best seen in FIG. 8, each clip member is fastened to its insert at only three points, namely, points 71a', 71b' and 71e', in a manner similar to that illustrated in FIG. 3, but with a triangular space 68' at one end rather than the rectangular space 68 of FIG. 3. At the distal end of the jaw, the clip member 70' is fastened to the tip engaging member 64' at the point 71e, so that the clip member is fastened to the insert at only three points, thereby facilitating its breaking away from the insert. Also, because the darts 80' are closer to the clip members 70' and 71' and the tip engaging collar 64' is anchored with dart-like members 106, there is a greater support of the clip members, facilitating the breakaway of the clip members 70' and 71' after the clip members have been locked together by the closing of the hemostat jaws and their subsequent opening. In all other respects clip members 70' and 71' and inserts 50' and 90' function in the manner described with respect to the embodiment of FIGS. 1 to 6.

Figure 5:
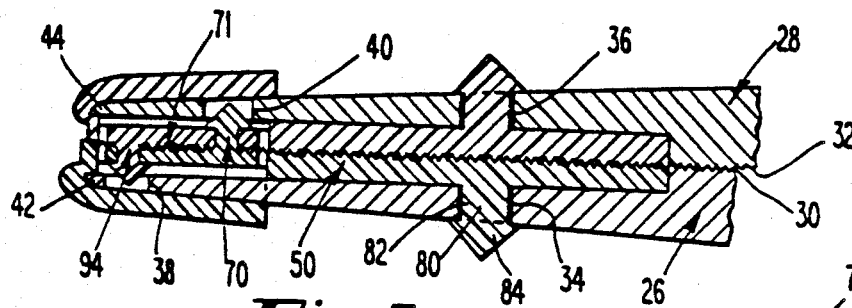
FIG. 5 is a vertical cross-sectional view of the jaws and inserts of FIG. 2 in the locked position, after the jaws have been closed on a blood vessel, nerve or other anatomical structure.

In the embodiment of FIGS. 7 and 8, it may be desired to form tip engaging member 64' as a sleeve, in the manner illustrated in FIGS. 2 and 5, to avoid the possibility of losing the tip engaging member when the clip members 70' and 71' break away from inserts 50' and 90'.

It may also be desirable to form insert 50' with upper surface 54' and serrations 56' in a manner similar to surface 54 and serrations 56 of FIG. 2 through 6 wherein clip members 70' and 71' would be surrounded by surface 56' but separated from said surface by spaces 66' similar to spaces 66 of FIG. 3.

Illustrated in FIG. 9 is another modification of the insert of the invention, substantially the same as that of FIGS. 1 to 6, but adapted for use on a hemostat having curved jaws. In this instance, the only difference is that the hemostat jaws 26" and 28" (not shown) are curved, the corresponding cut-outs 52" (not shown) in the jaws to accommodate the inserts 50" would be curved, and the inserts 50" themselves could also be curved. The clip members 70" and 71" (not shown) could remain linear, as in FIGS. 7 and 8, or curved as in FIG. 9. The insert 50" of FIG. 9 could, if desired, be substantially identical to the insert of FIG. 3, as illustrated, or of any of the other embodiments.

Figure 20:
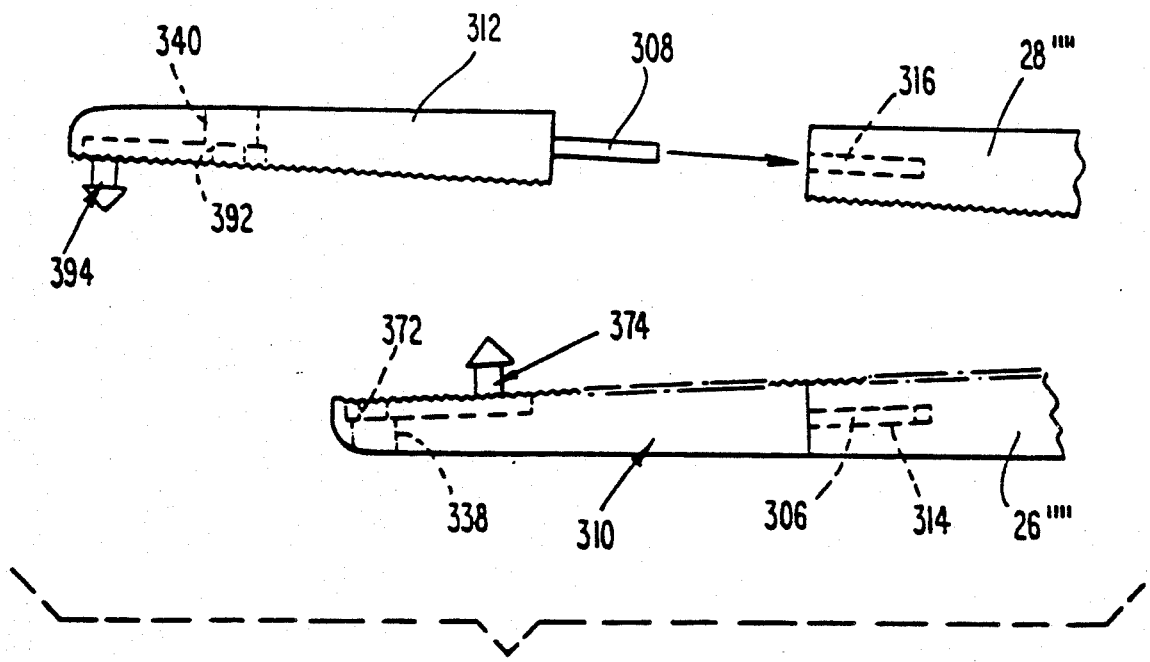
FIG. 20 is a partial side elevational view of another embodiment of jaw insert of this invention.
Figure 21:
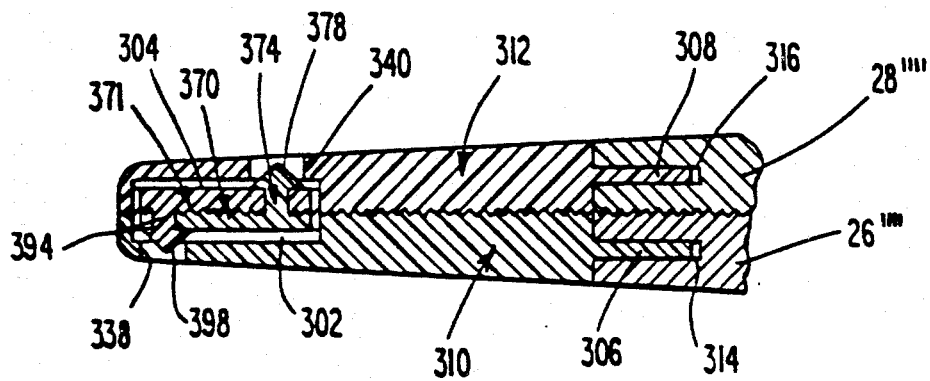
FIG. 21 is a cross-sectional view of the insert of FIG. 20, with the jaws in the closed position.

FIG. 10 shows schematically another embodiment of the hemostat of the invention, of a type further illustrated in FIGS. 20 and 21. The hemostat of FIG. 10 has shortened, flat-ended jaws 26''' and 28''', and the inserts 210 and 212 form the distal end of the jaws. In this embodiment, the metal jaw portions 26''' and 28''' are formed with suitable non-circular cross-section male members, respectively designated 206 and 208, and the inserts 210 and 212 are formed with corresponding mating apertures 214 and 216, so that the male members tightly and securely fit in the apertures. Male members 206 and 208 respectivley, which are of non-circular cross-section, lockingly seat in the corresponding apertures 214 and 216 in the inserts 210 and 212. Male members 206 and 208 and apertures 214 and 216 may, if desired, be formed with "snap-in" locking means to provide a more secure engagement of the jaws and inserts. The inserts 210 and 212 are shown schematically in FIG. 10 and the clip members and other details are not illustrated therein. However, the clip members incorporated in inserts 210 or 212 of FIG. 10 could be any of the embodiments illustrated herein or any other clip construction within the purview of this invention.

In FIGS. 20 and 21 there is illustrated an embodiment of the invention, similar to that of FIG. 10, wherein the hemostat jaws 26'''' and 28'''' are cut short and the inserts 310 and 312 form the distal ends of the jaws 26'''' and 28''''. The hemostat jaws of this embodiment are formed with respective noncircular cross-section apertures 314 and 316 and male members 306 and 308 of the inserts 310 and 312 to seat in those apertures to secure removably the inserts to the hemostat jaws. In this embodiment of the invention, insertion and removal of the inserts 310 and 312 into the modified hemostat are particularly simple. A tight fit of male members 306 and 308 in apertures 314 and 316 may be facilitated by tapering the male members and apertures slightly. This tapering would also make the inserts easier to apply to the jaws. The male members 306 and 308 may also be formed with "snap-in" enlargements (not shown) to engage suitable enlargement (not shown) at the inner ends of apertures 314 and 316 to provide a positive locking connection.

In the embodiment illustrated in FIGS. 20 and 21, the clip members 370 and 371 are similar to the ones illustrated in FIGS. 3, 5 and 6. However, because there are no jaws of the hemostat extending in the area of the clip member, there is no need for male members and sleeves to lock the inserts to the hemostat jaws, since this function is done by the members 306 and 308. Therefore, in the embodiment of FIG. 21, the inserts are simpler than in the embodiment of FIGS. 1 to 6. The respective clip members 370 and 371 are formed in inserts 310 and 312 and are attached thereto, in breakaway fashion in four corners, similar to the manner illustrated in FIG. 3, for example. The clip member construction per se is otherwise identical to that illustrated in FIGS. 3, 5 and 6 with cut-out portions 338 and 340 formed in the inserts 310 and 312, respectively, to permit the heads 378 and 398 of male members 374 and 394 to pass through corresponding apertures 392 and 372 to seat in the locked position.

The clip members 370 and 371 are attached to the inserts 310 and 312 only at three or four corners, by thin perforated or non-perforated webs (not shown), so that they will break away from the inserts when the clip members are locked and the jaws opened. A small space, respectively 302 and 304, is present in each insert, to illustrate that the insert is not attached to, but is spaced from, the back of its clip member.

Once the inserts 310 and 312 have been secured to the hemostat jaws 26'''' and 28'''', the invention is used in the manner described with respect to the embodiment of FIGS. 1 to 6.

Viewing FIGS. 11 and 12, there is illustrated another embodiment of the surgical clip of the invention which uses two upstanding fingers 406 to lock the two clip members 402 and 404 in place. The surgical clip 400 comprises the two clip members 402 and 404. Clip member 402 is formed with a pair of integral, upstanding fingers 406, one at each end. Each finger 406 comprises an upstanding portion 408 and an end portion 410, each end portion 410 having lip portion 412, which is adapted to overlie and engage the underlying upper clip member 404.

The lip 412 is triangular and tapers inwardly and downwardly, so that as the upper clip segment 404 is lowered, its sides 422 force the fingers 406 outwardly until the upep clip member is in place, in the locking position illustrated in FIG. 12, at which time the resilience of fingers 406 causes them to spring inwardly so that lips 412 overlie top 420 of segment 404, and lips 412 lock the two clip members 402 and 404 in fastened position.

The clip members 402 and 404 have respective serrated inner surfaces 416 and 418 and the serrations may be staggered so that the peaks of the serrations 416 are opposite to the valleys of the serrations 418 to ensure a tight closure of a blood vessel or other anatomical structure by the clip.

The clip 400 is desirably utilized as part of an insert (not shown), such as, for example, the insert illustrated in FIGS. 1 to 6. In that instance, the clip members 402 and 404 would each be an integral part of an insert, for example units 50 and 90 of FIG. 2, and would be fastened thereto, in break-away manner, by connections at, for example, four corners. The closure of clip members 402 and 404 by fingers 406 would be sufficiently strong that, when the jaws of the hemostat to which the inserts are fastened are being pulled apart, the clip members 402 and 404 would break away from the respective inserts. The hemostat, in the case of the embodiment of FIG. 2, or the insert, if the clip construction 400 is used in the embodiment illustrated in FIGS. 20 and 21, for example, would contain a suitable recess in the upper jaw or insert, as the case may be, to allow for the seating of the ends 410 of the fingers 406.

It is not necessary that both fingers 406 be located on the lower clip member 402. Rather, they could both be located on the upper clip member 404. Depending upon what type of closure construction is desired, suitable space will have to be provided in the opposing hemostat or insert to allow the ends of the fingers 406 to be seated. It may also be desired to incorporate one or more additional fingers 406 on one or both of the clip members intermediate thei ends to prevent lateral motion of the clip.

Figure 23:
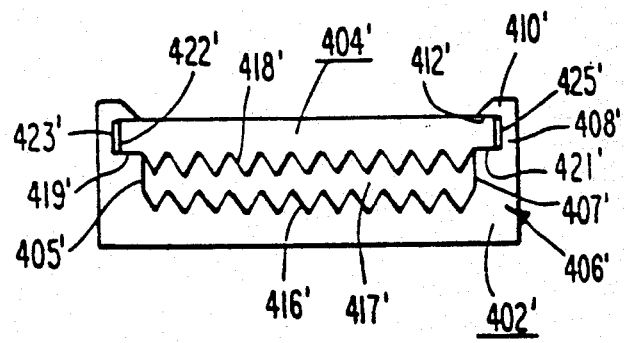
FIG. 23 is a side elevational view of another embodiment of the surgical clip of this invention similar to that illustrated in FIGS. 11 and 12, modified to include a separation in the locked position shown.

FIG. 23 illustrates another embodiment of the surgical clip substantially similar to the surgical clip generally designated 400 as shown in FIGS. 11 and 12. In this embodiment, however, the serrated surfaces 416' and 418' cannot touch. The serrations of these surfaces are such that peaks on one surface are juxtaposed to valleys on the other. Thus space labeled 417' is created and appears as a zig-zag opening. In operation clip members 402' and 404' perform in a manner similar to the operation of clip members 402 and 404 of FIG. 12 except that the two upstanding fingers 406' at each end of clip member 402' have a wide portion at each end designated 405' and 407' and a narrow portion 408'. This difference in size creates a shelf-like surface designated 419' and 421'. When clip member 404' is lowered it forces fingers 406' outward due to the triangular shape of lips 410'. Clip member 404' passes under said lips and the resilient fingers 406' move inwardly such that lips 412' lock the two clip members together. The height of portions 405' and 407' prevent clip 404' from continuing downward. Clip member 404' comes to rest on surfaces 419' and 421'. In practice the surgical clip illustrated in FIG. 23 will not apply as much pressure to the lumen of the occluded vessel. It is therefore useful in procedures where a minimum amount of trauma is desirable.

Figure 13:
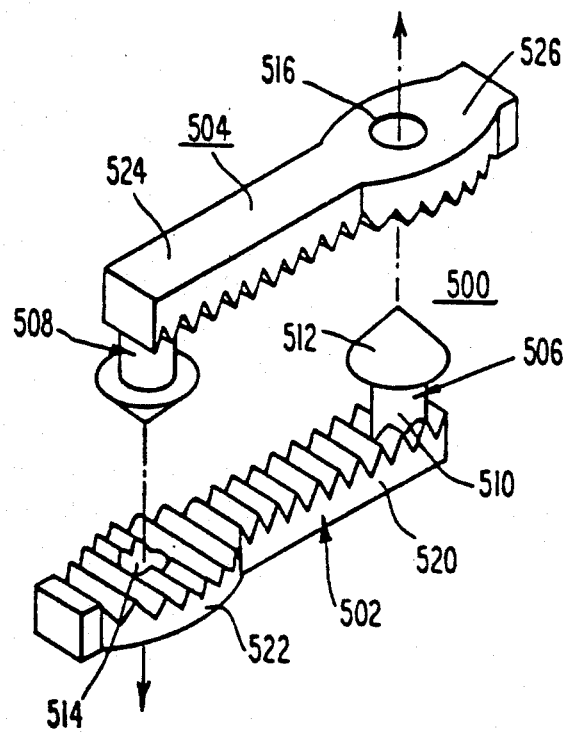
FIG. 13 is a perspective view of yet another embodiment of the surgical clip of this invention.

FIG. 13 illustrates yet another embodiment of surgical clip, generally designated by numeral 500, and including lower clip member 502 and upper clip member 504. As described more fully with respect to the embodiment of FIGS. 11 and 12, this clip would be part of a suitable insert, in the manner illustrated in FIGS. 1 to 6 or FIGS. 20 and 21, for example, and would be attached to the insert in a breakaway manner. In the embodiment of FIG. 13, each of the clip members 502 and 504 is seen to include a male member, respectively 506 and 508, each of which includes a vertical shaft 510 and head 512. The diameter of the heads 512 is somewhat larger than the diameter of the circular apertures, respectively designated 514 and 516, in the opposing clip members. In the illustrated embodiment, the heads 512 are conical.

In the embodiment illustrated in FIG. 13, the clip member 502 has a relatively narrow portion 520 and a somewhat circular, enlarged portion 522. Upper clip member 504 similarly has a relatively narrow portion 524 and an enlarged portion 526. The reason for having relatively narrow sections 520 and 524 is to provide as small and compact a clip as possible, whereas the enlarged portions 522 and 526 are necessary to provide requisite strength surrounding the aperture to be engaged by the opposing locking heat to ensure a firm lock.

Figure 14:
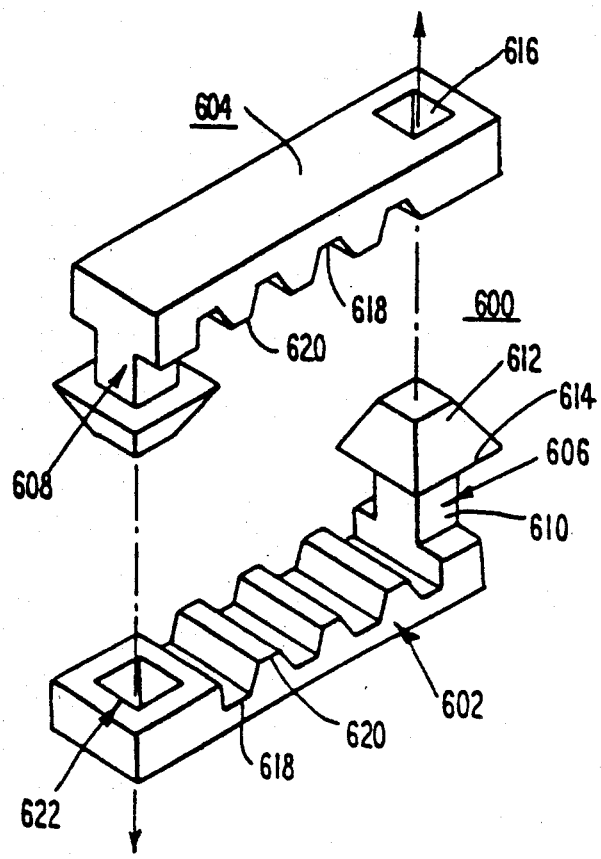
FIG. 14 is a perspective view, similar to Figure 13, of still another embodiment of the surgical clip of this invention.

FIG. 14 illustrates yet another embodiment of the clip of this invention, again intended to be utilized as part of an insert to be attached to a hemostat in the manner illustrated in FIGS. 1 to 6 or FIGS. 20 and 21. In the embodiment of FIG. 14, clip 600 comprises clip members 602 and 604, each of which is provided with a male member, respectively designated 606 and 608, and an opposing female aperture, respectively designed 616 and 622. The apertures are seen to be square in cross-section, rather than circular, as illustrated, for example, in FIG. 13. The male members 606 and 608 therefore have correspondingly shaped truncated-pyramidal head members 612, adapted to seat lockingly in the opposing apertures 616 and 622 of the mating clip members.

Rather than the pointed peaks and valleys of serrations, the serrations illustrated have flattened peaks and valleys 620 and 618. In the illustrated embodiment, a square head and flattened peaks and valleys may be desired because they reduce the prospect that a small piece of plastic would break off and become lodged in the patient's body and are easier to fabricate. Rounded peaks and valleys are also desirable because they would minimize tissue damage.

Surgical clips similar to those illustrated in FIGS. 4, 5, 6 and 11 and 14 were illustrated in FIGS. 22 and 23. The essential modification illustrated in FIGS. 22 and 23 was the incorporation of a feature whereby the two clip members could be lockingly joined together while retaining some physical space between their respective serrations thereby minimizing the trauma that the tighter fitting clips would produce. It is within the scope of this invention that all of the surgical clips presented herein could incorporate this feature. The purpose of FIGS. 22 and 23 was merely to illustrate its application to two of the surgical clips of this invention.

The embodiment of the invention illustrated in FIGS. 15 and 16 is substantially identical to that of FIGS. 7 and 8, except for the means utilized to fasten the inserts to the respective distal ends of the hemostat jaws 726 and 728. This embodiment illustrates another construction of the clip members or inserts to provide a secure and easy fastening of the inserts to the hemostat jaws. In the illustrated embodiment, each of clip members 770 and 771 is fastened at one end at two points to the corresponding inserts and is fastened at one point at its other end to the overhanging locking member 702, which extends through a cutout 704 in the tip of the respective jaw 726 or 728, as the case may be, releasably and lockingly engaging the respective upper and lower surfaces, as the case may be, of the jaws 726 and 728.

FIGS. 17, 18 and 19 illustrate yet another embodiment of the insert, similar to those illustrated in FIGS. 2, 3, 5, 7, 8, and 15 and 16, but providing a construction for fastening each insert to the tip of its corresponding hemostat jaw, respectively designated 826 and 828. In the embodiment of FIGS. 17, 18 and 19, each of the inserts has attached thereto, at one end, a pair of arrow-like pins 802 of circular cross-section with conical tips. The clip members 870 and 871 are fastened to the isnert in breakaway fashion by connecting portions 871a, 871b, 871c and 871d. The connecting portions 871a, 871b, 871c and 871d are similar to connecting portions 71a, 71b, 71c and 71d where clip member 70 is attached to insert 50 as in FIG. 3. The tip of the hemostat, as illustrated in FIG. 19, is formed with a pair of grooves 808 and 810, in which the bodies 804 of the pins 802 are seated, so that the pins snap in and lock the insert in place by virtue of the head 806 of the respective pins. In the drawings, two pins and grooves are illustrated for each insert, although more or fewer pins and grooves could desirably be utilized.

Figure 24:
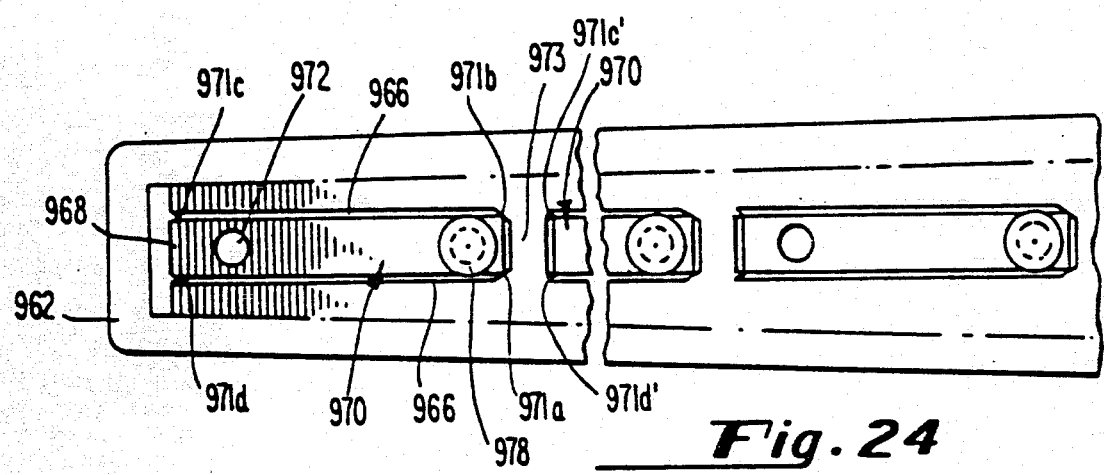
FIG. 24 is a broken top plan view of the lower jaw insert of an embodiment of this invention similar to that illustrated in FIGS. 1 to 6, modified to contain a plurality of clip members.

FIG. 24 illustrates yet another embodiment of the insert or clip assembly member of this invention. It functions in a manner similar to that presented in FIGS. 2 through 8 except that a plurality of clip members 970 are attached thereto rather than a single clip member 70. In practice clip members 970 will lockingly engage clip members 971 (not shown) when the hemostat jaws on which said inserts carrying said clip members are closed. In FIG. 24 the male members 978 have conical heads and shafts of cylindrical cross-section. Female apertures 972 are therefore accordingly circular also. The distance between adjacent clip members 973 is a matter of choice depending on the desired use. When the jaws of the hemostat containing said clip members are lockingly engaged and then removed, the clip members 970 will break away from clip assembly members illustrated in FIG. 24. If it is desired to have a line of clips with a large space between each clip, then space 973 would be large. If, on the other hand, it is desired that the line of clips be very close together, then space 973 can be made as small as desired. Space 973 could be reduced to zero in which case breakaway points 971a and 971b of the front clip member would also serve as breakaway points 971c' and 971d' for the second clip member 970 and so forth down the line.

In practice a surgeon would close the jaws of the hemostat having attached thereto inserts of the kind illustrated in FIG. 24. This closing would then create a line of occluding clips. The surgeon could then repeat the procedure parallel to the first line and produce a second series of clips, allowing him to sever the anatomical structure therebetween with only a minimal amount of leakage therefrom.

Figure 25:
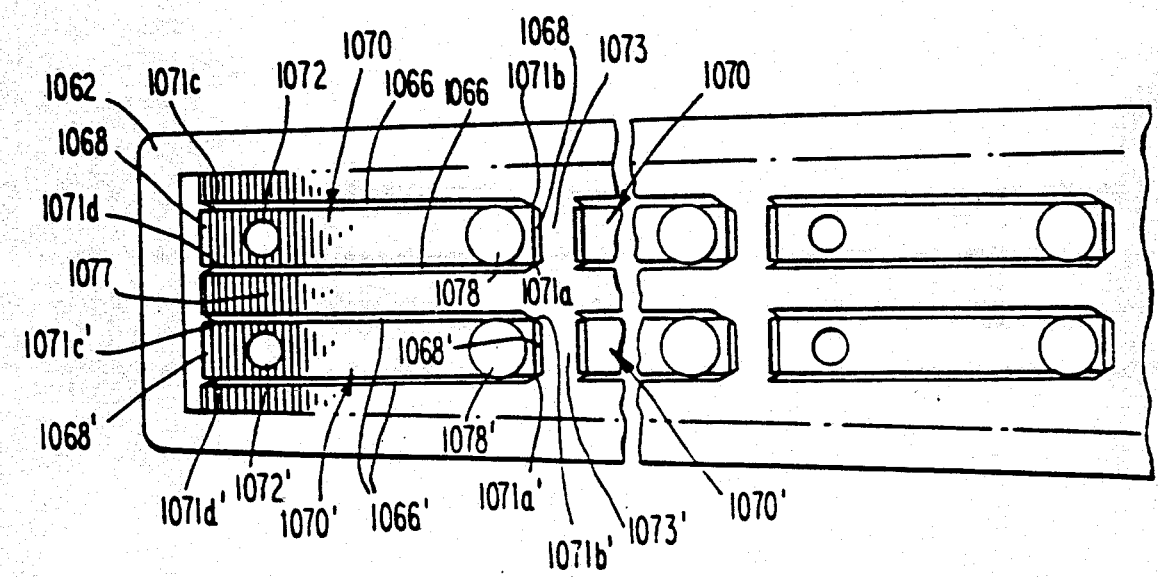
FIG. 25 is a broken top plan view of the lower jaw insert of an embodiment of this invention similar to that illustrated in FIGS. 1 to 6, modified to contain two rows of clip members.

FIG. 25 illustrates another embodiment of the insert of this invention which is similar to that illustrated in FIG. 24; however, instead of a single row of clip members attached to the insert there are two parallel rows of clip members attached to the insert. When the two jaws of a hemostat each containing an insert similar to that illustrated in FIG. 25 are closed about an anatomical structure, the two rows of clip members on each hemostat jaw will lockingly interengage and the opening of said hemostat jaws will cause two rows of surgical clips to be engaged about said anatomical structure. The proximity of the clip member 1070 to each other could be varied by varying spaces 1073 as described for the insert represented in FIG. 24. Furthermore, the distance between the adjacent rows could also be varied by varying space 1077. Clip members 1070 and 1070' could be moved close enough together so that the vacant space 1066 adjacent to space 1077 and vacant space 1066' also adjacent to space 1077 would coincide. Then the breakaway points 1071a and 1071d of clip member 1070 would then coincide with breakaway points 1071c' and 1071b' of clip 1070'.

It will be appreciated that the dimensions of the clip can be varied considerably to accommodate the particular application for which the clip is used. For example, blood vessels for which the clip could be used come in greatly varying sizes, and the clip would desirably be produced in a number of different sizes and shapes (for example, they could be curved or straight), for use with different sizes and shapes of hemostats, to accommodate to particular purposes for which the clip is being used. The particular sizes and shapes of clips can be varied within broad ranges and will be readily apparent to the skilled artisan. For example, if the clip is to be used for tubal ligation, its dimensions would be substantially greater than would be the case if it were used to tie off small blood vesesls in the brain or in pediatric surgery or to approximate fascia or to mark areas of neoplasia. In addition, the clip members could be formed with different types of inner faces than the serrations illustrated since many different face designs are known in the art.

In a clip utilized to tie off small blood vessels, the length of the clip member would be about 3 mm. or more, the maximum length depending on its purpose. Its width would be about 0.5 mm. or more.

In the embodiments of the invention, the surgical clip members of the invention have been illustrated as part of an insert which is part of a modified hemostat mechanism and this composition is, indeed, the preferred method of application of the clip formed by the joined clip members of the invention. It is, however, within the purview of the invention that the clip members be formed in individual unites, without the use of inserts or the modified hemostat mechanisms illustrated and applied by the use of hemostats alone with manual insertion in the hemostats. This method would be cumbersome and is not, however, the preferred form of the invention.

In the practice of the process of the invention, a modified hemostat is most desirably utilized. The modified hemostat may be of the type illustrated in FIGS. 1 to 6, for example, where the metal hemostat jaws extend to the ends of the insert, or the type illustrated in FIGS. 20 and 21, for example, where the inserts are firmly fastened to shortened hemostat jaws and in fact form an extension of the hemostat jaws. The inserts are fastened to the respective hemostat jaws, desirably in advance of any surgical procedure, and a series of loaded hemostats of various sizes and shapes of inserts, as needed, are located in a suitable accessible location in the operating room.

When a surgical procedure has progressed to the point where the surgical clip is required to ligate a blood vessel or other anatomical structure, such as a Fallopian tube, the surgeon or other medical professional would grasp the applicable size and shape of hemostat, with the inserts already in place, and place the open jaws of the hemostat so that the clip members of the insert are on opposite sides of the anatomical structure to be ligated. The handles of the hemostat would then be closed to lock the jaws of the hemostat closed by the engagement of conventional locking members, and the blood vessel or other tubular structure is then closed. If it is desired initially to leave the hemostat in place until a later time, the hemostat can be left in place with the jaws of the hemostat locked over the closed anatomical structure, to be removed at a later time.

When it is desired to remove the hemostat (which may be immediately after the jaws are closed) leaving a locked clip in place, the handles of the hemostat are moved to unlock the handle locking members and the handles are then separated to separate the jaws of the hemostat. When the hemostat jaws are initally closed, the respective male locking members entered or engaged the corresponding female locking members to lock the clip members to each other with the anatomical structure securely ligated therebetween. When the jaws of the hemostat are opened, the force necessary to separate the locked clip members or to separate the inserts from the jaws is stronger than the force necessary to break the breakaway portions which hold the clip members to the inserts. Accordingly, when the jaws are opened, the joined clip members breakaway from their corresponding inserts, and there remains in place a closed, locked properly positioned surgical clip securely ligating the anatomical structure. The inserts are then manually removed from the modified hemostat.

As has been noted, it may be desired to apply the clip so that the male locking members thereof actually pierce the tissue of the structure being occluded to ensure a better fastening of the clip on the anatomical structure and to prevent sliding of the clip along the longitudinal axis of the anatomical structure.

The embodiments of this invention have been presented with each clip assembly member or insert having only a single clip member attached thereto; however this presentation has been used for the simplicity that it achieves in the detailed explanations of the embodiments of this invention. It is contemplated and within the perview of this patent that each clip assembly member or insert could contain more than one clip member as illustrated in FIGS. 24 and 25. For example, the clip assembly member illustrated in FIGS. 20 and 21 could contain a plurality of clip members as shown in FIGS. 24 and 25. The advantages of multiple clip member inserts is obvious. It is therefore contemplated that such multiple clip assembly members are within the scope of this patent.

Although the invention has been described with respect to use with humans, it will be appreciated that the invention can also be used for performing surgical procedures in other animals.

The particular materials from which the clip and insert are formed are a matter of choice, so long as they are reasonably economical to fabricate, are safe and effective and possess the desired characteristics to allow the two clip members to lock in place satisfactorily and to ligate the anatomical structure closed.

It may be desired to form the hemostat and insert as a single unit of plastic material, which may be discarded in its entirety after the surgical clip has been locked in place and it is within the purview of this invention to do so. In that event, the inserts would not have to be separately handled and placed in locked positions in the hemostat jaws.

If the surgical clip is to dissolve in the body fluids, after a period of residence in vivo, it may be fabricated of a material which is slowly absorbable in the body fluids, such as collagen, gelatin, albumin, dried blood or synthetic soluble materials. In that event, it might be desired to fabricate the clip and insert of different materials and fasten the clip members in the inserts by the use of small amounts of properly placed adhesives, which will release upon the opening forces of the hemostat jaws.

Although the jaws, clips and inserts are illustrated as having serrated inner surfaces, it is within the scope of this invention for those surfaces to be planar or to have other linear or non-linear configurations than the serrations illustrated, so long as the blood vessel or other anatomical structure is sufficiently firmly held between the clip members.

In applying the surgical clips of this invention, it is preferable to use applicators which closely resemble conventional types of hemostats. However, other shapes and types of applicators may be used, if desired, without departing from the scope of this invention.

The clip members of this invention could be used for purposes other than ligating anatomical structures. For example, radioopaque clip members could be used to approximate fascia, mark areas of neoplasia or otherwise tag or mark areas of tissue not readily accessible by other means.

There are disclosed herein the preferred embodiments of the invention, although it will be appreciated that the particular shapes, dimensions, materials and similar characteristics of the invention may be varied without parting from the spirit and scope of this invention.

What is claimed is:

1. An article adapted to be attached removably and lockingly to a pair of opposed jaws of an applicator, comprising:
    (a) A pair of opposed, elongated plastic clip assembly members, each defining an elongated aperture;
    (b) Each clip assembly member having integral means lockingly to interconnect that clip assembly member to a jaw of an applicator;
    (c) Each clip assembly member having an inner surface, said inner surfaces being adapted to oppose each other;
    (d) At least two plastic clip members, one seated in the elongated aperture of one clip assembly member and the other seated in the elongated aperture of the other clip assembly member;
    (e) Shearable plastic web means releasably securing each clip member to its corresponding clip assembly member;
    (f) Each clip member, web means and clip assembly member comprising a unitary structure of one material; and
    (g) Each clip member having integral locking means whereby two opposing clip members lockingly interengage about an anatomical structure when said clip members are pressed together.

2. An article as set forth in claim 1, wherein said first named means comprises at least one locking means proximate to one end of each of said clip assembly members wherein it lockingly engages and forms an extension of said hemostat jaws.

3. An article as set forth in claim 1, wherein said first-named means comprises at least one locking means proximate each end of said clip assembly member.

4. An article as set forth in claim 1, wherein the inner surface of each clip member and the inner suface of its corresponding clip assembly member are substantially coplanar and each of said surfaces have a non-planar face formed therein to facilitate grasping of an anatomical structure.

5. An article as set forth in claim 1, wherein each said clip assembly member has a sleeve at one end adapted to engage the distal end of a hemostat jaw and a male member proximate its other end adapted lockingly to engage in an aperture in a hemostat jaw and wherein each said clip member is fastened to its clip assembly member by a plurality of thin webs of material, each of said clip members having a locking member proximate each end to lockingly engage the other clip member.

* * * * *